United States Patent [19]
Laitinen et al.

[11] Patent Number: 5,263,094
[45] Date of Patent: Nov. 16, 1993

[54] METHOD OF AND AN EQUIPMENT FOR OPTICAL INSPECTION OF STRIP AND SHEET PRODUCTS

[75] Inventors: Toni Laitinen; Timo Piironen, both of Oulu, Finland

[73] Assignee: Rautaruukki Oy, Oulu, Finland

[21] Appl. No.: 705,621

[22] Filed: May 28, 1991

[30] Foreign Application Priority Data

Jun. 7, 1990 [FI] Finland .................................. 902842

[51] Int. Cl.⁵ .......................... G06K 9/00; H04N 7/18
[52] U.S. Cl. ......................................... 382/8; 382/53; 382/41; 358/106
[58] Field of Search ................... 382/8, 53, 27, 41, 56; 358/106, 108, 426, 261.1

[56] References Cited

U.S. PATENT DOCUMENTS

| | | | |
|---|---|---|---|
| 4,665,317 | 5/1987 | Ferriere et al. | 358/106 |
| 4,751,572 | 6/1988 | Baumbaugh et al. | 358/133 |
| 4,908,871 | 3/1990 | Hara et al. | 382/8 |

FOREIGN PATENT DOCUMENTS 311990 4/1989 European Pat. Off. .
368460 5/1990 European Pat. Off. .

Primary Examiner—Joseph Mancuso
Assistant Examiner—Yon J. Couso
Attorney, Agent, or Firm—Sughrue, Mion, Zinn, Macpeak and Seas

[57] ABSTRACT

A method of and an equipment for optical inspection of strip and sheet products for the detection of surface defects, which equipment comprises an image forming apparatus 1, 2 for producing images of successive parts of the surface of a product 3 and for converting the images to analog signals 4, an A/D converter 5 for converting the analog signal to a digital signal 6, and an image analyzing unit 7 for analyzing the digital signal to detect surface defects therefrom. To reduce the data processing capacity required of the image analyzing unit, the equipment further comprises a compression unit 8 arranged between the A/D converter and the image analyzing unit for compressing the digital signal before it is analyzed.

4 Claims, 2 Drawing Sheets

METHOD OF AND AN EQUIPMENT FOR OPTICAL INSPECTION OF STRIP AND SHEET PRODUCTS

BACKGROUND OF THE INVENTION

The present invention relates to a method of and an equipment for optical inspection of strip and sheet products for the detection of surface defects, which method comprises producing images of successive parts of the surface of a product, converting the images produced to an analog signal on the basis of the brightness of pixels, converting the analog signal to a digital signal by providing each pixel with a digital value representing its brightness, analyzing the digital signal for the detection of surface defects on the product and giving information of the surface defects detected.

A method of detecting surface defects on a moving strip, similar to the one described above, is known from U.S. Pat. No. 4,665 317. By means of such an equipment, it is possible to alarm the operating personnel when substantial surface defects appear, and moreover, to produce necessary inspection reports. An introduction of automatic inspection equipments like this has been based firstly on the fact that it is problematic to get manpower capable enough of doing this kind of work of a very monotonous nature, and secondly on the fact that an inspection carried out by a man is not at all possible any more when the strip speeds are increasing. The increased strip speeds and also the desire to provide an image as detailed as possible of the defects possibly occurring on the strip create a need to increase also the processing capacity of the automatic inspection equipment. The problem will then be the number of the operations needed. The fact is that if a 1500 mm broad strip moving at the speed of 300 m/min is inspected with the image dot size being 1 mm, the system shall be capable of analyzing 7.5 millions of image dots per second. In practice, it is possible to provide without excessive costs an equipment capable of doing 1.5 millions of image dot operations per second. However, such a speed requires already that relatively expensive equipments are used. If a further increase of the capacity of the equipment were desired, it would be necessary to acquire several equipments like this expensive as such and to place them adjacent to each other, each equipment arranged to inspect only a part of the strip width.

SUMMARY OF THE INVENTION

The object of he present invention is to provide a method and an equipment by means of which it is possible either to increase the inspection capacity or, alternatively, to simplify the equipment carrying out the inspection, without the quality of the inspection suffering therefrom, however. This is achieved by means of the method of the invention, which is characterized in that it further comprises compressing the digital signal before an analysis thereof.

This compression can take place in such a manner that the value of each pixel is compared with n/2 preceding and n/2 following pixel values and it is replaced by the minimum or the maximum value observed at the comparison, depending on whether the surface defects show dark or light from the surroundings, and every nth value is selected from the sequence of values obtained in this way to be used for the production of the compressed signal.

Alternatively, the pixels are divided at the compression into groups of n successive pixels and from each group is each time selected the one of the maximum or the minimum value, depending on whether the surface defects show dark or light from the surroundings, to be used for the production of the compressed signal. From a group of n successive pixels is preferably selected the one of the minimum or the maximum value by at first comparing the two first pixels with each other and by selecting from them the smaller/greater one and by comparing this with the following pixel and by selecting from them the smaller/greater one, and so on, the result of the comparison with the last pixel of the group being the pixel of the minimum or the maximum value searched for.

At an image signal compression effected by methods of the kind described above, an original signal is replaced by a signal containing the most substantial features of the original signal. It is thus certain that also the compressed signal includes all the information substantial for the inspection. If the compression is effected in the direction of pixel lines transverse to the strip, the information of the real width of a surface defect is lost at the compression. This width is, however, of no significance for the detection of a surface defect or even for the classification thereof. If the method is applied both in the transverse and the longitudinal direction of the strip, the information of the length of surface defects is also lost, which makes the classification of surface defects more difficult. Consequently, such a two-dimensional compression is not necessarily desirable, though possible.

The equipment of the invention for optical inspection of strip and sheet products for the detection of surface defects comprises an image forming apparatus for producing images of successive parts of the surface of a product and for converting these images to an analog signal, an A/D converter for converting the analog signal to a digital signal and an image analyzing unit for an analysis of the digital signal in order to detect surface defects and to bring them to the user's knowledge. This equipment is characterized in that it further comprises a compression unit arranged between the A/D converter and the image analyzing unit for the compression of the digital signal before it is analyzed.

According to a first embodiment of the invention, the compression unit comprises n delay elements connected in series and n reference units connected in series and a register arranged after the nth reference unit, the series connection of the delay elements being arranged to receive the output signal of the A/D converter and the series connection of the reference units also being arranged to receive the output signal of the A/D converter, while each reference unit additionally receives the output signal of the corresponding delay element in order, and the register being arranged to deliver every nth signal value to its output.

According to a second embodiment of the invention, being especially advantageous with respect to a realization of the invention as an integrated circuit, the compression unit comprises a series connection of a multiplexer, a delay element and a register, the multiplexer being arranged to receive the digital signal coming from the A/D converter and the output signal of the delay element, and a comparator arranged to receive the signal coming from the A/D converter and the output signal of the delay element, to compare these with each other and to control the multiplexer on the basis of the result of the comparison and a control logic arranged to control the register to deliver every nth signal value to its output and the comparator to control, irrespective of the comparison carried out thereby, the multiplexer to deliver every n+1st signal value to its output.

BRIEF DESCRIPTION OF THE DRAWINGS

In the following, the method and the equipment of the invention are described in greater detail referring to the enclosed drawing, in which.

DETAILED DESCRIPTION OF THE PREFERRED EMBODIMENTS

Figure 1:
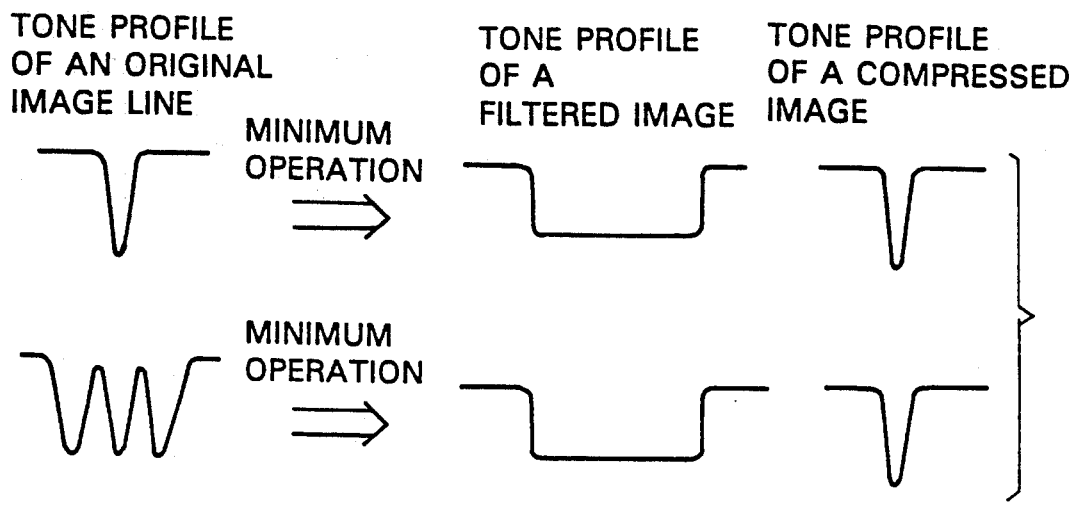
FIG. 1 shows a change in the tone profile of an image line in connection with a compression according to the invention.

FIG. 1 shows the influence of a compression used in the optical inspection method according to the invention on the information to be processed. The upper example of FIG. 1 presents a case in which the brightness of some pixel is substantially lower than that of the others, i.e. the strip to be inspected shows a dark area at this point. When to this tone profile at first is applied the alternative of the method of the invention, according to which the value of each pixel is compared with n/2 preceding and n/2 following pixel values and it is replaced by the minimum value observed at the comparison, a tone profile similar to that shown in FIG. 1 under the title "tone profile of a filtered image" is obtained, in which tone profile n pixels have the same tone value as the pixel of the lowest tone value of the original image line. When every nth value is then picked according to the invention from this tone profile, a tone profile shown to the right in FIG. 1 under the title "tone profile of a compressed image" is obtained, which tone profile substantially corresponds to the original tone profile, even if the number of pixels included in this tone profile only is the nth part of the number of pixels of the original tone profile. Thus is observed that no substantial information is lost in connection with an individual surface defect.

The lower example of FIG. 1 presents a case in which there are several surface defects within a short area. When the above procedure is applied to this tone profile, a tone profile is obtained in which all n pixels have been provided with the tone value of the pixel of the lowest tone value. This tone profile is shown in the middle part of FIG. 1. When every nth value is then picked from this tone profile, the tone profile shown to the right in FIG. 1 is obtained. Further, from this tone profile can reliably be seen the existence of a surface defect, but in this tone profile, however, several original surface defects have been united into one surface defect. Thus, the information of the width of the original surface defect has been lost at the compression. This width of the surface defect is, however, of no substantial significance for the detection of surface defects or for the classification thereof either, when a classification of surface defects on metal strips or sheets is concerned. In practical cases, n can be some integer, for instance within the range 4 to 32, even if very high values of n are not necessarily advantageous when the compressed image shall be examined also visually, e.g. by means of a television monitor.

Figure 2:
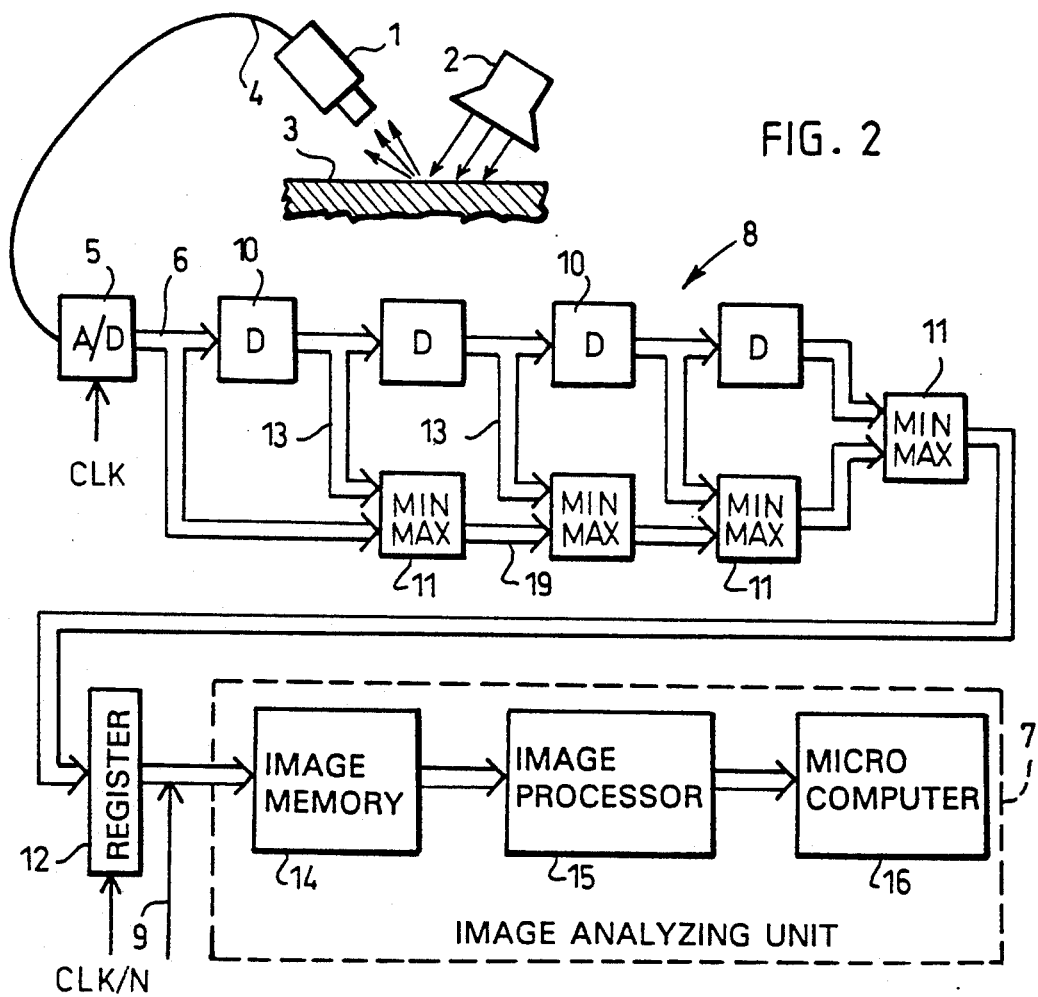
FIG. 2 shows a block diagram of an equipment according to a first embodiment of the invention.

FIG. 2 shows an equipment for the realization of a method as described in FIG. 1. Firstly, the equipment comprises an image forming apparatus consisting of a video camera 1 of line or matrix type and an illumination device 2 for the illumination of a surface 3 to be inspected. By means of this image forming apparatus, images are produced of successive parts of the surface and converted to an analog video signal 4. This analog video signal is analog/digital converted by means of an A/D converter 5 to obtain a digital signal 6. After this, this digital signal 6 is compressed by means of a unit 8 to obtain a compressed signal 9 before the signal is analyzed by means of an image analyzing unit 7. This image analyzing unit 7 comprises an image memory 14, an image processor 15 and a micro computer 16 connected in series. Because the image is preserved in "image form" (matrix form) at the compression, without the structure of the image being broken or changed into a substantially different format, image analyzing units planned to be used for processing an uncompressed signal can be used. By means of such image analyzing units, it is possible, firstly, to detect deviations to be interpreted as surface defects from the compressed digital signal 9 and, secondly, to provide the necessary alarms and reports on the inspection of the strip. An image analyzing unit like this is marketed for instance by Rautaruukki Oy with the designation SMARTVIS. Because this image analyzing unit is conventional per se and does not constitute a special object of the present invention, it will not be described in greater detail in this connection.

For the most substantial part, the invention is formed by the image signal compression unit 8. In the exemplifying embodiment of FIG. 2, this compression unit 8 comprises four delay elements 10 connected in series and four reference units 11 connected in series, respectively, and a register 12 for picking ever 4th pixel from the digital signal fed thereto. The delay of each delay element 10 corresponds to one clock cycle of a clock CLK coming to the analog/digital converter 5. The series connection of the delay elements 10 relates to the series connection of the reference units 11 in such a way that to each reference unit is fed, firstly, a signal 19 of the preceding reference unit, and secondly, an output signal 13 of the delay element 10 with the corresponding order number. This reference unit then selects from these two input signals either the smaller or the greater one, depending on whether the surface defects in this case show light or dark from the surroundings. This selected value is then fed by the reference unit 11 to the output 19 thereof. In this manner, each signal starting from the output of the last reference unit 11 has the value of the pixel of the minimum or the maximum value found among the values of 4 successive pixels, as has been described with reference to FIG. 1. These successive values in digital form are then fed to the register 12 clocked with a clock frequency CLK/n, which in the example of FIG. 2 is CLK/4, the digital signal 9 to be obtained from its output containing every 4th digital value from the sequence of values fed into the register 12. In this way, the image signal has been compressed to a form containing a quarter of the number of pixels included in the original digital signal 6. So, the image analyzing unit 7 can be realized either by means of equipments slower and thus simplier than before or by means of a conventional image analyzing unit, which now makes it possible to inspect an area 4 times wider than previously per time unit.

Figure 3:
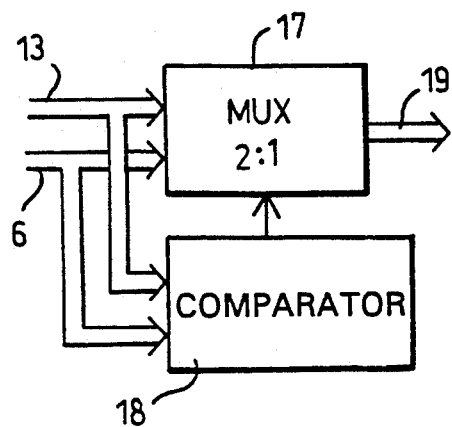
FIG. 3 shows the structure of a reference unit included in the equipment of FIG. 2 in greater detail.

FIG. 3 shows the structure of the reference unit 11 included in the block diagram of FIG. 2 in greater detail. This reference unit comprises a multiplexer 17 and a comparator 18. These two receive both the digital signal 13 coming from the delay element 10 and the digital signal 6, if it is the first comparator, or the output signal 19 of the preceding comparator. The comparator 18 compares these values with each other and selects from them either the greater or the smaller one, depending on whether a pixel of the lowest or the highest value is searched for. On the basis of the comparison, the comparator 18 controls the multiplexer 17, which has stored both in its input signal, in such a way that the value found on the basis of this comparison is brought to the output 19 of the multiplexer. Thus the multiplexer 17 is of type 2:1, receiving two simultaneous input signals and delivering only one of them forward.

Figure 4:
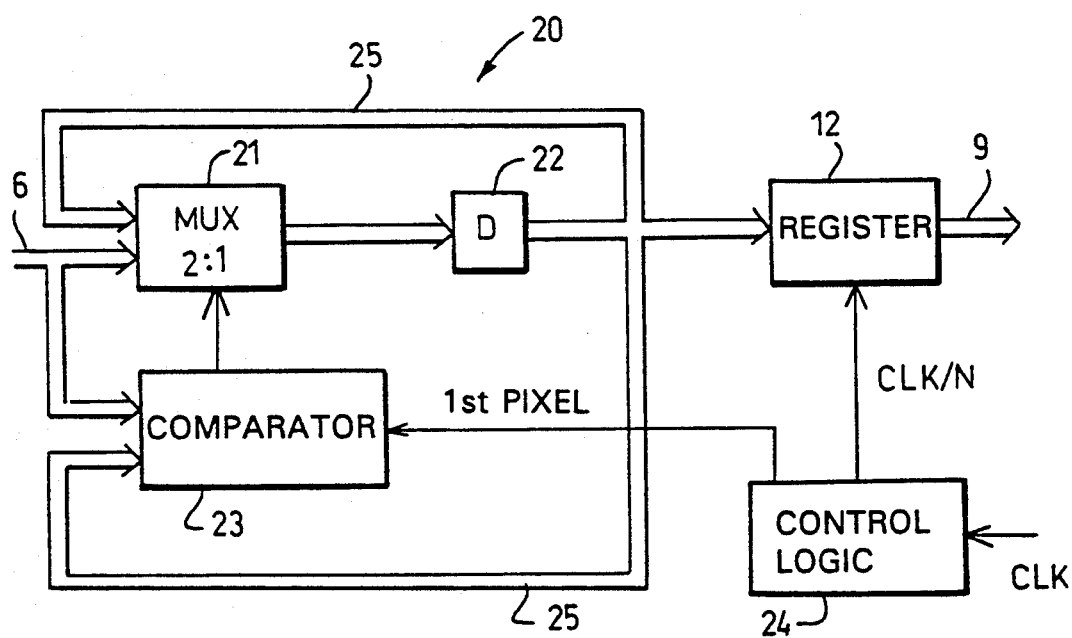
FIG. 4 shows a block diagram of a compression unit included in an equipment of a second embodiment of the invention.

FIG. 4 shows a compression unit 20 suitable for being used instead of the compression unit 8 of FIG. 2 and more easily realizable as an integrated circuit than the compression unit 8 shown in FIG. 2, especially when the value of n increases. It is a fact that the number of both delay elements and reference units in the structure of FIG. 2 is equal to n, while the number of components in the structure of FIG. 4 does not need to be changed according to the value of n, but only the manner in which the circuit is controlled.

At its input, the compression unit 20 of FIG. 4 receives the digital signal 6 to be obtained from the analog/digital converter 5. At its output, it delivers the compressed digital signal 9 corresponding to the compressed digital signal 9 to be obtained in the embodiment of FIG. 2. The compression unit 20 comprises a series connection of a multiplexer 21, a delay element 22 and a register 12, as well as a comparator 23 arranged to control the multiplexer 21. As appears from the reference numerals, the register 12 corresponds substantially to the register 12 included in the compression unit 8 of FIG. 2. In the compression unit 20 of FIG. 4, the multiplexer 21 receives both the digital signal 6 and a signal 25 fed back from the output of this multiplexer 21 through the delay element 22. The comparator 23 receives also the digital signal 6 and the output signal 25 of the delay element 22. This comparator 23 selects from these inputs the greater or the smaller one, depending on whether the surface defects show dark or light against the background, and controls the multiplexer 21 on the basis of the result of the comparison by delivering to its output the value selected on the basis of the selection of the comparator 23. This value is brought to the delay element 22, the delay of which corresponds to one clock cycle. The output 25 of this delay element 22 is brought besides to the multiplexer 21 and the comparator 23 mentioned above also to the register 12, which is controlled by means of a control logic 24 to deliver every nth signal value to its output 9. This control logic 24 controls also the comparator 23 in such a way that the multiplexer 21 can be made to deliver to its output, irrespective of the result of the comparison, the value of the first pixel from a group each including n pixels, irrespective of the value of the last pixel of the preceding group including n pixels. In this manner, the compression unit of FIG. 4 performs a measure, in which the pixels are divided into groups of n successive pixels and from each group is in each particular case selected the one of the maximum or the minimum value, depending on whether the surface defects show dark or light from their surroundings. In the compression unit 20, this minimum or maximum pixel from a group of n successive pixels is selected by at first comparing the two first pixels with each other and by selecting from them the smaller/greater one and by comparing this with next pixel and by selecting from them the smaller/greater one, and so on, the result of the comparison carried out with the last, i.e. the nth, pixel of the group being the pixel of the minimum or the maximum value from this group of n pixels searched for.

Two exemplifying methods and equipments have been described above for carrying out a desired compression of a digital image signal. It is understandable that the same result can be provided also in manners somewhat deviating from the procedures or structural solutions described above, without deviating from the scope of protection defined by the enclosed claims, however. Additionally, the methods and equipments described above could further be complemented by parts capable of providing a two-dimensional compression of the image signal, to which has been referred already in some degree. Such a compression could be realized by collecting to a suitable memory a sufficient number of compressed digital signals 9 and by performing a new compression of these signals in such a manner that the compression would now be effected by comparing each compressed pixel with adjacent pixels seen in the longitudinal direction of the strip. Thus, the two-dimensional area of the surface to be inspected could now be represented by means of one pixel. Such a two-dimensional compression is, however, out of the question, if a loss of information about the real range of a surface defect is not desired in either direction of compression.

I claim:

1. A method of optical inspection of strip and sheet products for the detection of surface defects, which method comprises:
   producing images of successive parts of the surface of a product,
   converting the images produced to an analog signal on the basis of the brightness of pixels,
   converting the analog signal to a digital signal by providing each pixel with a digital value representing its brightness, comprising the digital signal,
   analyzing the compressed digital signal for the detection of surface defects on the product, and
   giving information of the surface defects detected, wherein at the compression the brightness value of each pixel is compared with n/2 preceding and n/2 following pixel brightness values in a scanning direction, and replaced by one of the minimum and the maximum brightness value observed at the comparison, depending on whether the surface defects show dark or light from their surroundings, and every nth value is selected from the sequence of values thus obtained and used for the production of the compressed signal.

2. An equipment for optical inspection of strip and sheet products for the detection of surface defects, comprising: an image forming apparatus (1, 2) for the production of images of successive parts of the surface of a product (3) and for the conversion of the images to an analog signal (4), an A/D converter (5) for the conversion of the analog signal to a digital signal (6), a compression unit (8; 20) for the compression of the digital signal from th A/D converter, and an image analyzing unit (7) for analyzing the digital signal to detect surface defects therefrom, wherein the compression unit (8) comprises n delay (10) connected in series and n reference units (11) connected in series, and a register (12) arranged after the nth reference unit, the series connection of the delay units being arranged to receive the digital signal (6) from the A/D converter and the series connection of the reference units also being arranged to receive the digital signal from the A/D converter, each reference unit additionally receiving an output signal (13) of a corresponding delay unit in order, and the register being arranged to output every nth signal value.

3. A method of optical inspection of strip and sheet products for the detection of surface defects, which method comprises:
producing images of successive parts of the surface of a product,
converting the images produced to an analog signal on the basis of the brightness of pixels,
converting the analog signal to a digital signal by providing each pixel with a digital value representing its brightness,
compressing the digital signal,
analyzing the compressed digital signal for the detection of surface defects on the product, and
giving information of the surface defects detected, wherein at the compression the pixels are divided into groups of n successive pixels, and one of the maximum and the minimum pixel brightness value is selected from each group, depending on whether the surface defects show dark or light from their surroundings, to be used for the production of the compressed signal, wherein from a group of n successive pixels one of the minimum and the maximum pixel brightness value is selected by comparing the first two pixel values with each other and selecting a smaller or greater one, by comparing the selected pixel value with the following pixel value and selecting a smaller or greater one, and so on, the result of the comparison with the last pixel of the group being the pixel of the minimum or the maximum value searched for.

4. An equipment for optical inspection of strip and sheet products for the detection of surface defects, comprising: an image forming apparatus for the production of images of successive parts of the surface of a product (3) and for the conversion of the images to an analog signal (4), an A/D converter (5) for the conversion of the analog signal to a digital signal (6), a compression unit (8,20) for the compression of the digital signal from the A/D converter, and an image analyzing unit (7) for analyzing the digital signal to detect surface defects therefrom, wherein the compression unit (20) comprises a series connection of a multiplexer (21), a delay element (22) and a register (12), the multiplexer being arranged to receive the digital signal (6) from the A/D converter and an output signal (25) of the delay element, and a comparator (23) arranged to receive the digital signal (6) from the A/D converter and the output signal of the delay element, and to control the multiplexer on the basis of the result of the comparison, and a control logic (24) arranged to control the register to output every nth signal value and the comparator to control, irrespective of the comparison performed by it, the multiplexer to deliver every n+1st signal value to its output.

* * * * *